(12) United States Patent
Tong

(10) Patent No.: US 7,005,087 B2
(45) Date of Patent: Feb. 28, 2006

(54) COMPOSITION AND METHOD FOR PREVENTING FOULING IN (METH)ACRYLIC ACID PROCESSES

(75) Inventor: David Youdong Tong, Houston, TX (US)

(73) Assignee: Nalco Energy Services, L.P., Sugar Land, TX (US)

( * ) Notice: Subject to any disclaimer, the term of this patent is extended or adjusted under 35 U.S.C. 154(b) by 268 days.

(21) Appl. No.: 10/748,725

(22) Filed: Dec. 30, 2003

(65) Prior Publication Data

US 2005/0139807 A1 Jun. 30, 2005

(51) Int. Cl.
*C09K 15/16* (2006.01)
*C07D 233/16* (2006.01)
*C07D 27/40* (2006.01)
*C07C 57/18* (2006.01)

(52) U.S. Cl. .................. 252/401; 548/348.1; 548/546; 562/598

(58) Field of Classification Search ................... None
See application file for complete search history.

(56) References Cited

U.S. PATENT DOCUMENTS 6,461,440 B1  10/2002  Sutoris et al.

FOREIGN PATENT DOCUMENTS

GB            1318874       *   5/1973

* cited by examiner

*Primary Examiner*—Paul A. Zucker
(74) *Attorney, Agent, or Firm*—Michael B. Martin; Thomas M. Breininger

(57) ABSTRACT

A composition comprising aminoalkyl imidazoline or alkyl-substituted succinimide antifoulants or mixtures thereof, and use of aminoalkyl imidazolines and alkyl-substituted succinimides to prevent fouling in (meth)acrylic acid manufacturing processes and processes in which (meth)acrylic acid is used in a reaction and where unreacted (meth)acrylic acid is recovered.

17 Claims, No Drawings

COMPOSITION AND METHOD FOR PREVENTING FOULING IN (METH)ACRYLIC ACID PROCESSES

TECHNICAL FIELD

This invention relates to a composition and method of preventing fouling in (meth)acrylic acid processes. More particularly, this invention is a composition comprising aminoalkyl imidazoline or alkyl-substituted succinimide antifoulants or mixtures thereof, and use of the antifoulants to prevent fouling in (meth)acrylic acid manufacturing processes and processes in which (meth)acrylic acid is used in a reaction and where unreacted (meth)acrylic acid is recovered.

BACKGROUND OF THE INVENTION

The most common route to (meth)acrylic acid is through gas phase catalytic oxidation of alkanes, alkenes, alkanols or alkenals containing 3 to 4 carbon atoms. The reaction products from the oxidation process are separated, and (meth)acrylic acid is purified in the recovery and purification section. The design of the recovery and purification section varies in process equipment and operating conditions, but, fundamentally it comprises extraction and distillation separations. In a generalized (meth)acrylic acid recovery and purification process, the effluent from the oxidation process is cooled in an absorber to remove the light components in the product effluent. Then, in the extraction column, (meth)acrylic acid is concentrated through removal of either water or acetic acid or both with a selected solvent. The crude (meth)acrylic acid stream is then purified of remaining extraction solvent and reaction by-products in succeeding distillation towers. Design variations exist with solvent selection.

(Meth)acrylic acids are reactive monomers, and they tend to polymerize with any trivial environment change. This is the case during the recovery and purification operation in manufacturing (meth)acrylic acid, where elevated temperatures accelerate the polymerization of (meth)acrylic acid. Under such circumstances, the undesired polymerization becomes so severe that polymer deposition fouls process equipment. Eventually, equipment shutdown and cleaning is required for removal of the polymeric foulant. Conventionally, polymerization inhibitors are used in the manufacturing processes of the monomers to prevent this undesired polymerization. Typical polymerization inhibitors are phenolic compounds, amines, quinones, nitroxyl compounds and certain inorganic complexes. Phenothiazine (PTZ), hydroquinone (HQ) and monomethyl hydroquinone ether (MEHQ) are examples of the most widely used inhibitors. These inhibitors are designed to interrupt the polymerization reactions and prevent the formation of the polymer. However, none of the available polymerization inhibitors are efficient enough to completely eliminate undesired polymer formation. Even in the presence of these inhibitors, polymer formation and subsequent fouling is still substantial, so that periodic cleaning is part of routine (meth)acrylic acid processes.

In industrial practice, dispersants may also be used in addition to polymerization inhibitors to improve fouling prevention. Dispersants are usually comprised of molecules with an affinity to the foulant particle surface and good solubility in the liquid process stream. Unlike inhibitors, dispersants do not interfere with the polymerization reactions involved in foulant formation. Instead, dispersant molecules adsorb on preexisting polymer particles, through chemical or physical interaction, and form an insulating layer on the polymer particles, which prevent the particles from agglomerating, thereby keeping them suspended in the process media. The selection of an effective dispersant remains as an experimental art because their utility is highly dependant on the detailed nature of the foulant material and liquid medium, both of which are unique to a given process.

SUMMARY OF THE INVENTION

In an aspect, this invention is a composition comprising (meth)acrylic acid and one or more of the compounds selected from the group consisting of aminoalkyl imidazolines of formula (I)

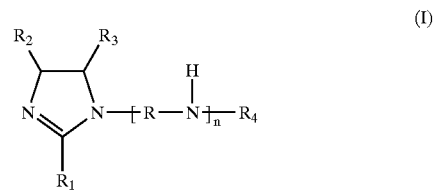

and alkyl-substituted succinimides of formula (II)

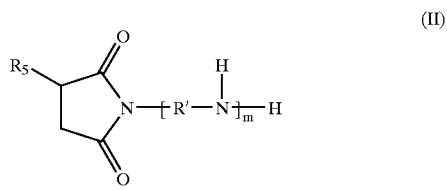

and mixtures thereof wherein n is an integer of 1 to about 9; m is an integer of 1 to about 10; R and R' are $C_1$–$C_6$ alkylene; $R_1R_2R_3$ and $R_5$ are independently selected from $C_1$–$C_{30}$ alkyl, alkenyl, aryl, alkylaryl, arylalkyl, aminoalkyl, and aminoaryl; and wherein $R_4$ is selected from hydrogen, $(CH_2)_2$ COOH, $CH_2CH(CH_3)COOH$, imidazoline, alkyl and alkylaryl.

In another aspect, this invention is a method of preventing fouling in a (meth)acrylic acid process comprising adding to the process stream an effective antifouling amount of one or more aminoalkyl imidazolines of formula (I)

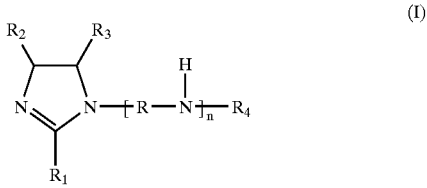

or one or more alkyl-substituted succinimides of formula (II)

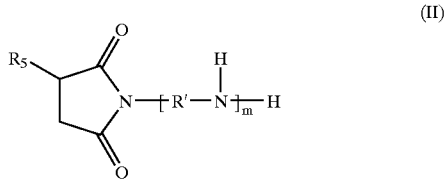

(II)

or a mixture thereof wherein n is an integer of 1 to about 9; m is an integer of 1 to about 10; R and R' are $C_1$–$C_6$ alkylene; $R_1R_2R_3$ and $R_5$ are independently selected from $C_1$–$C_{30}$ alkyl, alkenyl, aryl, alkylaryl, arylalkyl, aminoalkyl, and aminoaryl; and $R_4$ is selected from hydrogen, $(CH_2)_2COOH$, $CH_2CH(CH_3)COOH$, imidazoline, alkyl and alkylaryl.

The aminoalkyl imidazolines and alkyl-substituted succinimides of this invention effectively prevent the formation and deposition of foulant materials on process equipment used in producing (meth)acrylic acid, or in related processes where (meth)acrylic acid is contained in the process stream.

DETAILED DESCRIPTION OF THE INVENTION

Definitions of Terms

"Alkenyl" means a monovalent group derived from a straight or branched chain hydrocarbon containing 1 or more carbon-carbon double bonds by the removal of a single hydrogen atom. The alkenyl group may be interrupted with one or more oxygen or sulfur atoms, or one or more groups of formula —$NY^1$— where $Y^1$ is defined herein, provided that no two oxygen or sulfur atoms or —$NY^1$— groups are attached to one another. Representative alkenyl groups include ethenyl, propenyl, butenyl, 1-methyl-2-buten-1-yl and the like.

"Alkoxy" means an alkyl-O— group where alkyl is defined herein. Representative alkoxy groups include methoxy, ethoxy, propoxy, butoxy, and the like.

"Alkyl" means a monovalent group derived from a straight or branched chain saturated hydrocarbon by the removal of a single hydrogen atom. The alkyl group may be interrupted with one or more oxygen or sulfur atoms, or one or more groups of formula —$NY^1$— where $Y^1$ is defined herein, provided that no two oxygen or sulfur atoms or —$NY^1$— groups are attached to one another. Representative alkyl groups include ethyl, n- and iso-propyl, n-, sec-, iso- and tert-butyl, lauryl, octadecyl, and the like.

"Alkylaryl" means an alkyl-arylene-group where alkyl and arylene are defined herein. Representative alkylaryl include tolyl, ethylphenyl, propylphenyl, nonylphenyl, and the like.

"Alkylene" means a divalent group derived from a straight or branched chain saturated hydrocarbon by the removal of two hydrogen atoms. Representative alkylene groups include methylene, ethylene, propylene, isobutylene, and the like.

"Amino" means a group of formula $Y^1Y^2N$— and quaternary salts thereof where $Y^1$ and $Y^2$ are independently hydrogen, alkyl, aryl, heterocyclyl or arylalkyl as defined herein. $Y^1$ and $Y^2$, together with the N atom to which they are attached may also form a heterocyclyl group. Representative amino groups include amino (—$NH_2$), methylamino, ethylamino, iso-propylamino, tert-butylamino, dimethylamino, diethylamino, methylethylamino, piperidino, and the like.

"Aminoalkyl" means an amino-alkylene-group wherein amino and alkylene are defined herein. Representative aminoalkyl groups include 3-dimethylaminopropyl, dimethylaminoethyl, and the like.

"Aminoaryl" means an amino-arylene-group where amino and arylene are defined herein.

"Aryl" means substituted and unsubstituted aromatic carbocyclic radicals and substituted and unsubstituted aromatic heterocyclic radicals having about 5 to about 14 ring atoms. Representative aryl include phenyl naphthyl, phenanthryl, anthracyl, pyridyl, furyl, pyrrolyl, quinolyl, thienyl, thiazolyl, pyrimidyl, indolyl, and the like. The aryl is optionally substituted with one or more groups selected from hydroxy, halogen, $C_1$–$C_4$ alkyl and $C_1$–$C_4$ alkoxy.

"Arylalkyl" means an aryl-alkylene-group wherein aryl and alkylene are defined herein. Representative arylalkyl include benzyl, phenylethyl, phenylpropyl, 1-naphthylmethyl, and the like.

"Arylene" means an aromatic monocyclic or multicyclic ring system derived from an aryl as defined herein by the removal of two hydrogen atoms.

"Heterocyclyl" means an aromatic or non-aromatic monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred ring sizes of rings of the ring system include about 5 to about 6 ring atoms. The heterocyclyl is optionally substituted by one or more hydroxy, alkoxy, amino or thio groups. Representative saturated heterocyclyl rings include piperidyl, pyrrolidinyl, piperazinyl, morpholinyl, thiomorpholinyl, and the like. Representative aromatic heterocyclyl rings include pyrazinyl, pyridyl, pyrimidinyl, isoxazolyl, isothiazolyl, pyrazolyl, pyrrolyl, pyrazolyl, triazolyl, and the like.

"Hydroxyalkyl" means an alkyl group as defined herein substituted by one or more to hydroxyl groups, provided that no more than one hydroxy group may be attached to a single carbon atom of the alkyl group. Representative hydroxyalkyl include hydroxyethyl, 2-hydroxypropyl, and the like.

"(Meth)acrylamide" means acrylamide and methacrylamide.

"(Meth)acrylic acid" means methacrylic acid and acrylic acid.

"(Meth)acrylic acid process" means processes for manufacturing acrylic acid and methacrylic acid, particularly the recovery and purification processes of the manufacturing process. (Meth)acrylic acid process also include processes in which (meth)acrylic acid is used in a reaction and where unreacted (meth)acrylic acid is recovered, such as esterification of (meth)acrylic acid. Also included are other manufacturing processes in which (meth)acrylic acid occurs as a significant by-product and is present in the initial stages of purification of the manufactured product, for example, acrolein and acrylonitrile manufacture.

"Preventing" includes both preventing and inhibiting.

Preferred Embodiments

This invention discloses the use of selected aminoalkyl imidazoline and alkyl-substituted succinimide antifoulants to mitigate the fouling on the process equipment in handling (meth)acrylic acid or (meth)acrylic acid containing process streams.

Aminoalkyl imidazolines may be prepared by reacting a long chain carboxylic acid with a polyalkylene polyamine in a stoichiometric manner as described, for example, in U.S. Pat. Nos. 2,200,815, 2,267,965, 2,992,230 and 5,300,235, incorporated herein by reference.

Long chain carboxylic acids use to prepare the aminoalkyl imidazolines of this invention have formula R"—COOH wherein R" is $C_2$–$C_{30}$ alkyl or alkenyl, optionally substituted with one or more aryl groups. Representative long chain carboxylic acids include oleic, linoleic, conjugated linoleic, palmitic, and stearic acids.

Polyalkylene polyamines used to prepare the aminoalkyl imidazolines of this have formula

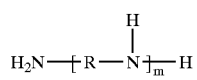

where R is $C_1$–$C_6$ alkylene and m is an integer of 1 to about 11. "Polyehtylene polyamine" means a polylakylene polyamine where R is —$CH_2CH_2$—. Representative polyalkylene polyamines include diethylene triamine, triethylene tetramine, tripropylene tetramine, tetraethylene pentamine, and pentaethylene hexamine.

In a preferred aspect of this invention, the aminoalkyl imidazoline is prepared by reacting tall oil fatty acid (TOFA), a mixture of oleic and linoleic acids with an equimolar amount of diethylene triamine (DETA) to provide TOFA/DETA imidazoline (1-aminoethyl-2-$C_{17}$ alkylene-2-imidazoline).

In another preferred aspect the aminoalkyl imidazoline is prepared by (i) reacting tall oil fatty acid with a polyethylene polyamine; and (ii) reacting the product of step (i) with acrylic acid.

The preparation of alkyl-substituted succinimides and related materials is described in, for example, U.S. Pat. Nos. 3,172,892, 3,219,666, 3,272,746, 4,379,064 and 4,889,646, incorporated herein by reference. The term "succinimide" is understood to include many of amide, imide and amidine species produced as by-products of the reaction employed in preparation of a succinimide. The predominant products, however, is a succinimide, and the term has been generally accepted as meaning the product of the reaction of an alkenyl-substituted succinic acid or anhydride with a nitrogen-containing compound. Preferably, nitrogen-containing compounds are amines, and more preferably polyalkylene polyamines as defined above.

In a preferred aspect of this invention, the alkyl-substituted succinimide is prepared by reacting a mixture of $C_{12}$–$C_{30}$ olefins, maleic anhydride and polyethylene polyamine. "$C_{12}$–$C_{30}$ olefins" means the oligomers of $C_2$–$C_8$ α-mono-olefins such as the oligomers of ethylene, propylene, 1-butene, isobutene, and the like.

In another preferred aspect, the alkyl-substituted succinimide is prepared by reacting a mixture of $C_{12}$–$C_{30}$ olefins, maleic anhydride and diethylene triamine.

The aminoalkyl imidazoline and alkyl-substituted succinimide antifoulants of this invention can be used neat or as blends with a suitable solvent. For convenience of application (handling, injection and distribution), a suitable solvent is often preferred to formulate the antifoulant into liquid form. Suitable solvents should dissolve the antifoulants and must be compatible with the (meth)acrylic acid process. Suitable solvents include water, aliphatic distillates, acetic acid, acrylic acid, methacrylic acid, alkylacrylate esters, alkyl methacrylate esters, commercial extraction solvents in use with various (meth)acrylic acid production processes, and aromatics. Representative extraction solvents include butyl acetates, heptane, diisobutyl ketone, ethyl acrylate, methyl isobutyl ketone, high boiling oils, and the like. Representative aromatics include xylene, toluene, heavy aromatic naphthas, and the like.

In a preferred aspect of this invention, the aminoalkyl imidazoline and alkyl-substituted succinimide antifoulants are used in combination with one or more polymerization inhibitors. Polymerization inhibitors are conventionally used to suppress undesired polymerization in (meth)acrylic acid production. Examples of polymerization inhibitors include HQ, MEHQ, PTZ, 4-hydroxyl-2,2,6,6-tetramethylpiperidino-1-oxyl, other nitroxyl compounds, N-alkylphenylenediamines, nitrosated N-alkylphenylenediamines, hydroxylamines, nitrosophenylhydroxylamines, nitrosodiphenylamine, copper complexes, manganese complexes, and others known in the art of (meth)acrylic acid preparation, purification and storage/transport. In many cases multiple inhibitors have been used in combination in the (meth)acrylic acid process. The term "process polymerization inhibitor" means any use, singly or in combination, of known polymerization inhibitors.

In another preferred aspect of this invention, the aminoalkyl imidazoline and alkyl-substituted succinimide antifoulants are used in combination with one or more dispersant antifoulants. Representative dispersant antifoulants include sulfonated hydrocarbons such as dodecyl benzenesulfonate, poly isobutylene succinic acid esters, alkylphenolethoxylates, alkylphenolformaldehyde resins, fatty acid esters, fatty acid amides, fatty alcohol ethoxylates, polysaccharide esters, and the like. This is especially important when a fouling situation partially originates from fouling sources other than polymerization of (meth)acrylic acid. An improvement in antifoulant performance is expected through a combination of the antifoulants described in the present invention with other potential dispersants.

In another preferred aspect of this invention the the aminoalkyl imidazoline and alkyl-substituted succinimide antifoulants are used in combination with one or more polymerization inhibitors and one or more dispersant antifoulants.

The aminoalkyl imidazoline and alkyl-substituted succinimide antifoulants of this invention are preferably used to inhibit fouling in (meth)acrylic acid processes selected from (meth)acrylic acid manufacturing processes, (meth)acrylic acid esterification processes, acrolein manufacturing processes and acrylonitrile manufacturing processes.

The aminoalkyl imidazoline and alkyl-substituted succinimide antifoulants and any polymerization inhibitors, dispersant antifoulants and solvents are injected directly into the (meth)acrylic acid process, including injection at different locations into the process, as separate formulations injected at the same location, or injected together as part of a single combined formulation.

The aminoalkyl imidazolines and alkyl-substituted succinimides are preferably added to the process at a dosage of about 1 to about 10,000 ppm, more preferably at a dosage of about 10 to about 1000 ppm and still more preferaby at a dosage of about 30 to about 300 ppm.

In a preferred aspect of this invention, the aminoalkyl imidazolines and alkyl-substituted succinimides are added continuously.

In another preferred aspect, the aminoalkyl imidazolines or alkyl-substituted succinimides are added intermittently.

The foregoing may be better understood by reference to the following examples, which are presented for purposes of illustration and are not intended to limit the scope of the invention.

Antifoulant performance of the aminoalkyl imidazoline and alkyl-substituted succinimide antifoulants of this invention is measured using a bench scale total reflux distillation unit to simulate the polymer forming environment in the distillation operation of purifying (meth)acrylic acid. The unit has a reflux condenser on the top, a tray section in the middle, and a 1 L boiler flask at the bottom. For an experiment with acrylic acid feed, the boiler flask is filled with about 450 g of acrylic acid, which is inhibited with about 200 ppm MEHQ. To ensure a safe operation, an additional amount of inhibitor, e.g., 0.23 g PTZ is added to the boiler flask. With constant heating applied from an electric heating mantle, the boiler flask boils the acrylic acid and generates inhibitor-deficient acrylic acid vapor. The vapor travels up through the tray section and into the reflux condenser. The tray section contains several equally-spaced circular sieve trays made out of stainless steel 316L. The acrylic acid condensate from the reflux condenser drips back through the trays to the boiler flask. The unit is operated under a pressure of 160 to 190 mm Hg and a pot temperature of 97–100° C.

Unless indicated otherwise, in each of the following examples the unit is operated in a total reflux mode for 30 minutes. A liquid additive, either an antifoulant-containing solution (treated) or a control solvent (untreated), is continuously injected into the unit at a location above the tray section. The injected solution mixes well with the reflux condensate before the condensate drains down into the tray section ensuring that the tray section is in good contact with the injected additive.

In the untreated experiment, polymer forms and precipitates out on the trays with time. Polymer also precipitates out on the boiler flask inner wall above the liquid and at the bottom of the flask.

In a treated experiment, all antifoulants are compared at equivalent dosages on a weight to weight basis. Compared with an untreated experiment, an effective antifoulant results in less polymer accumulation on the tray section, on the flask wall and in the flask liquid.

Qualitative measure of polymer precipitation is through visual inspection of polymer adhesion on the trays and walls. Quantitative measure is obtained by weighing the polymer on the tray section at the end of each experiment.

EXAMPLE 1

Untreated Control

This experiment is terminated after 21 minutes of reflux operation due to severe fouling and plugging of the tray section. White polymeric foulant is found on both sides of each metal tray, with somewhat more mass adhered to the higher trays. The holes on the top tray are completely blocked with polymer. Polymer (4.5 g) is collected on the tray section during this experiment. Polymer precipitation is also observed on the boiler flask wall above and under the liquid line.

EXAMPLE 2

Treatment with TOFA/DETA Imidazoline

This experiment is performed as described in Example 1, except that an antifoulant, TOFA/DETA imidazoline, is continuously injected.

The TOFA/DETA imidazoline is prepared by reacting TOFA with DETA in 1:1 mole ratio. Following a typical imidazoline preparation procedure, DETA is gradually added to a TOFA containing solution at a temperature of about 70° C. with constant stirring. A temperature increase is usually seen during the addition. Once the DETA addition is complete, the mixed solution is heated to about 175° C. and the temperature is maintained until the theoretical amount of water is collected for amide formation. The mixture solution is then heated to about 225° C. and maintained for two hours. Additional water is collected at this temperature due to the formation of imidazoline. The resulting product is an aminoethyl $C_{17}$ alkenyl imidazoline with a characteristic infrared spectrum band around 1610 $cm^{-1}$.

At the end of the experiment, most parts of the metal trays are clean of any polymer, except for a few of small polymer clusters scattered underneath the metal trays, probably due to insufficient contact of the antifoulant solution to the surfaces at these spots. Polymer (0.5 g) is collected on the tray section, and the flask wall and the liquid in the flask are clean and clear. Table 1 compares the treated experiment with the untreated one in terms of average fouling rate. The average fouling rate is calculated by averaging the final polymer on the tray section over the experiment duration. The comparison shows a significant reduction in fouling rate with the antifoulant treatment (from 0.21 for the untreated to 0.017 g per minute for the treated). This example clearly demonstrates that the TOFA/DETA imidazoline is an effective antifoulant for acrylic acid polymerization induced deposition.

EXAMPLE 3

Treatment with Oleic Acid/DETA Imidazoline

This treated experiment is performed as described in Example 2, except that the TOFA/DETA imidazoline treatment is replaced with an oleic acid/DETA imidazoline. The oleic acid/DETA imidazoline is prepared by reacting oleic acid with DETA in 1:1 mole ratio according to the procedure described in Example 2.

At the end of the experiment, most parts of the metal trays are clean, except for several polymer clusters formed at the edges of some of the trays, probably due to insufficient contact of the antifoulant to the surfaces at those locations. Polymer (3.1 g) is collected on the tray section. The flask wall and the liquid are fairly clean and clear. The average fouling rate is 0.10 g per minute as shown in Table 1. Again, the oleic/DETA imidazoline treatment resulted in a considerable reduction in polymer formation and deposition.

EXAMPLE 4

Treatment with TOFA/DETA Imidazoline Adduct with Acrylic Acid

This experiment is performed as described in Example 2, except that the TOFA/DETA imidazoline is replaced with an adduct of TOFA/DETA imidazoline and acrylic acid. The TOFA/DETA imidazoline-acrylic acid adduct is prepared by reacting the TOFA/DETA imidazoline from Example 2 with an equimolar amount of acrylic acid at a temperature of about 120° C. under a constant nitrogen purge for 2.5 hours. The TOFA/DETA imidazoline—acrylic acid reaction produces a typical adduct of Michael Addition reaction product having the following formula:

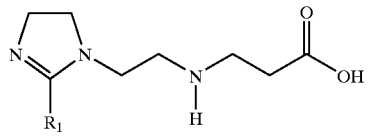

wherein $R_1$ is a $C_{17}H_{33}$ alkylene group.

At the end of the experiment, most parts of the metal trays are clean, and only a few of polymer clusters are seen under the metal trays. Polymer (0.6 g) is collected on the tray section. The average fouling rate for this experiment is 0.020 g per minute, which is comparable with the run treated with the TOFA/DETA imidazoline in Example 2.

EXAMPLE 5

Treatment with TOFA/Aminoethylethanolamine (AEEA) Imidazoline

This experiment is performed as described in Example 2, except that the TOFA/DETA imidazoline is replaced with a TOFA/AEEA imidazoline. The TOFA/AEEA imidazoline is prepared by reacting TOFA with AEEA in 1:1 mole ratio following the procedure of Example 2. The resulting product is hydroxyethyl $C_{17}$ alkenyl imidazoline.

At the end of the experiment, most surfaces of the metal trays are covered with polymer. Polymer (5.6 g) is collected on the tray section. Polymer deposition is also seen on the flask wall and at the bottom of the flask. The average fouling rate for this experiment is 0.19 g per minute, comparable with the untreated one in Example 1. Unlike the TOFA/DETA imidazoline in Example 2, the TOFA/AEEA imidazoline treatment did not provide any significant improvement in fouling reduction. This example suggests that the amino functional group is critical for the observed performance with TOFA/DETA imidazoline.

EXAMPLE 6

N-diethylene Triamine $C_{12}$–$C_{30}$ Alkenyl Succinimide Treatment

This experiment is performed as described in Example 2, except that a N-diethylene triamine $C_{12}$–$C_{30}$ alkenyl succinimide is used in place of the TOFA/DETA imidazoline. The succinimide is prepared by reacting a mixture of $C_{12}$–$C_{30}$ olefins, maleic anhydride and diethylene triamine using the typical reaction conditions described below.

A $C_{12}$–$C_{30}$ olefin mixture and maleic anhydride are charged in a reactor and heated at about 250° C. for about three hours to form a $C_{12}$–$C_{30}$ alkenyl succinic anhydride. Diethylene triamine is then slowly added to the reactor. A solvent is usually added with the diethylene triamine to reduce the viscosity increase due to the reaction. An exotherm typically raises the reactor temperature as the amine is added. The reaction temperature is maintained at about 140° C. for about two hours to finish the reaction. The final reaction product is the N-diethylene triamine $C_{12}$–$C_{30}$ alkenyl succinimide.

At the end of the experiment, the top surfaces of the metal trays are clean from polymer, and the underneath surfaces of the metal trays are scattered with loose polymer clusters. 2.8 g of polymer is collected on the tray section. The flask wall and the liquid are fairly clean and clear. The calculated average fouling rate is 0.093 as given in Table 1. It is clear that the N-diethylene triamine $C_{12}$–$C_{30}$ alkenyl succinimide treatment is effective in the fouling prevention.

TABLE 1

Fouling Rates for an Untreated Acrylic Acid Process and an Acrylic Acid Process Treated with Representative Aminoalkyl Imidazoline and Alkyl-Substituted Succinimide Antifoulants

| antifoulant | Operation time | Foulant, g | Fouling rate, g/min |
|---|---|---|---|
| untreated | 21 | 4.5 | 0.21 |
| TOFA/DETA imidazoline | 30 | 0.5 | 0.017 |
| Oleic acid/DETA imidazoline | 30 | 3.1 | 0.10 |
| TOFA/DETA imidazoline-acrylic acid adduct | 30 | 0.6 | 0.020 |
| TOFA/AEEA imidazoline | 30 | 5.6 | 0.19 |
| N-ethyleneamine $C_{12}$–$C_{30}$ alkenyl succinimide | 30 | 2.8 | 0.093 |

Changes can be made in the composition, operation and arrangement of the method of the invention described herein without departing from the concept and scope of the invention as defined in the claims.

The invention claimed is:

1. A compound having the formula:

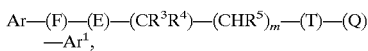

wherein

T is

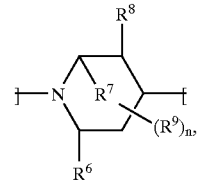

where $R^6$ is taken together with one of $R^7$ and $R^8$ to form a bridge of one to two bridgehead carbon atoms, and the other of $R^7$ and $R^8$ is selected from hydrogen and $R^9$;

Ar and $Ar^1$ are, each phenyl;

F is alkylene, alkenylene, or a bond;

E is selected from —C(=O)N($R^{10}$)—, —SO$_2$N($R^{10}$)—, —N($R^{11}$)C(=O)N($R^{10}$)—, —N($R^{11}$)SO$_2$N($R^{10}$)—, —N($R^{11}$)C(—S)N($R^{10}$)—, —N($R^{11}$)C(=O)—, —N($R^{11}$)SO$_2$—, —N($R^{12}$)C(=O)CH($R^{13}$)—, and CH($R^{13}$)C(=O)N($R^{12}$)—, where:

$R^{10}$, $R^{11}$, $R^{12}$, and $R^{13}$ are, independently of each other, hydrogen, alkyl, acyl, haloalkyl, cycloalkyl, cycloalkylalkyl, aryl, aralkyl, aralkenyl, heteroaryl, heteroaralkyl, heterocycloalkyl, heteroalkyl, or -(alkylene)-C(=O)-Z, where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

or alternatively, $R^{12}$ and $R^{13}$ may be taken together with the nitrogen and carbon atoms to which they are attached, respectively, to form a heterocyclyl or heteroaryl ring optionally substituted with up to two groups selected from $R^{14}$;

R³ and R⁴ are, independently of each other, hydrogen, alkyl, alkenyl, haloalkyl, cycloalkyl, cycloalkylalkyl, aryl, aralkyl, heteroaryl, heteroaralkyl, heterocyclyl, heterocyclylalkyl, heteroalkyl, -(alkylene)-C(=O)-Z¹, or -(alkylene)-C(O)₂Z¹, where Z¹ is alkyl, haloalkyl, alkoxy, haloalkyloxy, hydroxy, amino, mono- or disubstituted amino, aryl, aralkyl, aryloxy, aralkyloxy, heteroaryl, heteroaryloxy, or heteroaralkyloxy;

R⁵ is hydrogen or alkyl;

Q is —C(=O)— or C₁₋₂alkylene;

R⁹ is attached to any available carbon atom of ring T and is selected from lower alkyl, hydroxy, lower alkoxy, halo, cyano, trifluoromethyl, trifluoromethoxy, or a lower alkyl substituted with one of hydroxy, lower alkoxy, halo, cyano, trifluoromethyl, or trifluoromethoxy;

R¹⁴ is selected from lower alkyl, hydroxy, lower alkoxy, halo, cyano, trifluoromethyl, trifluoromethoxy, and a lower alkyl substituted with one of hydroxy, lower alkoxy, halo, cyano, trifluoromethyl, or trifluoromethoxy;

m is 0 or 1; and n is 0 to 4; and pharmaceutically acceptable salts thereof.

2. A compound according to claim 1, or a pharmaceutically acceptable salt thereof, wherein:

Ar and Ar¹ are both phenyl;

F is a bond;

E is selected from —C(=O)N(R¹⁰)—, —N(R¹¹)C(=O)N(R¹⁰)—, —N(R¹¹)C(=O)—, —N(R¹²)C(=O)CH(R¹³)—, and CH(R¹³)C(=O)N(R¹²)—, where:

R¹⁰, R¹¹, R¹², and R¹³ are, independently of each other, hydrogen or alkyl;

or alternatively, R¹² and R¹³ may be taken together with the nitrogen and carbon atoms to which they are attached, respectively, to form a heterocyclyl or heteroaryl ring optionally substituted with up to two groups selected from R¹⁴;

R³ and R⁴ are, independently of each other, hydrogen, alkyl, alkenyl, haloalkyl, heteroalkyl, or -(alkylene)-C(=O)-Z¹, where Z¹ is alkyl, haloalkyl, alkoxy, haloalkyloxy, hydroxy, ammo, mono- or disubstituted amino, aryl, aralkyl, aryloxy, aralkyloxy, heteroaryl, heteroaryloxy, or heteroaralkyloxy;

Q —CH₂—;

R⁹ and R¹⁴ are independently selected from methyl, ethyl, hydroxy, methoxy, halo, cyano, trifluoromethyl, or trifluoromethoxy; and n is 0 to 2.

3. A compound according to claim 1, or a pharmaceutically acceptable salt thereof, wherein T is selected from the group consisting of:

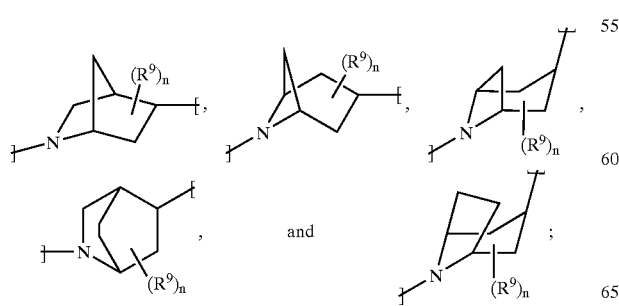

and R⁹ is any available carbon atom of ring T and is selected from lower alkyl and hydroxy, and n is 0 to 2.

4. A compound of claim 1, or a pharmaceutically acceptable salt thereof, wherein:

Ar is a phenyl ring optionally substituted with one, two or three substituents selected from alkyl, heteroalkyl, alkoxy, —COR¹⁵, —SO₂R¹⁷, methylenedioxy, hydroxy, halo, acylamino, amino, mono- or disubstituted amino, —CONR¹⁵R¹⁶, -(alkylene)-CONR¹⁵R¹⁶, —COOR¹⁵, -(alkylene)-COOR¹⁵ and/or —NR¹⁶SO₂R¹⁷;

R¹⁵ and R¹⁶ are each independently hydrogen or alkyl; and

R¹⁷ is alkyl, amino or mono or disubstituted amino.

5. A compound of claim 4, or a pharmaceutically acceptable salt thereof, wherein Ar is selected from phenyl, 4-chlorophenyl, 4-methylphenyl, 4-methoxyphenyl, 3-methylsulfonylphenyl, 3,5-dimethoxyphenyl, 3,4-dimethoxyphenyl, and 3,4,5-trimethoxyphenyl.

6. A compound of claim 1, or a pharmaceutically acceptable salt thereof, wherein F is a bond.

7. A compound of claim 1, or a pharmaceutically acceptable salt thereof, wherein E is —C(=O)N(R¹⁰)—, —N(R¹⁰)C(=O)N(R¹¹)—, or N(R¹²)C(=O)CH(R¹³)—, where R¹⁰ and R¹¹ are hydrogen or lower alkyl, and R¹² and R¹³ are taken together with the nitrogen and carbon atoms to which they are attached, respectively, to form

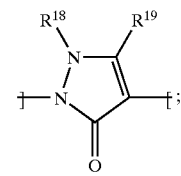

where R¹⁸ and R¹⁹ are selected from hydrogen and lower alkyl.

8. A compound of claim 7, or a pharmaceutically acceptable salt thereof, wherein E is

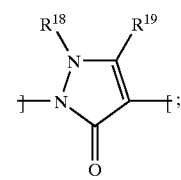

and m is 0.

9. A compound of claim 1, or a pharmaceutically acceptable salt thereof, wherein R³ is hydrogen; and R⁴ is hydrogen, methyl, ethyl, 1-methylethyl, isopropyl, 1-hydroxyethyl or 2-hydroxyethyl.

10. A compound of claim 1, or a pharmaceutically acceptable salt thereof, wherein R³ is hydrogen; and R⁴ is 1-methylethyl.

11. A compound of claim 1, or a pharmaceutically acceptable salt thereof, wherein T is

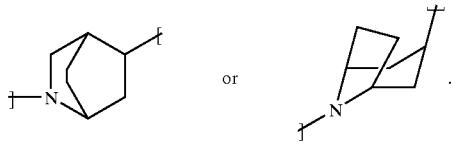

12. A compound of claim 1, or a pharmaceutically acceptable salt thereof, wherein Q is —CH$_2$—.

13. A compound of claim 1, or a pharmaceutically acceptable salt thereof, wherein:
Ar$^1$ is a phenyl ring optionally substituted with one, two or three substituent selected from alkyl, heteroalkyl, alkoxy, halo, trifluoromethyl, nitro, or mono- or disubstituted amino.

14. A compound of claim 1, or a pharmaceutically acceptable salt thereof, wherein:
Ar$^1$ is 4-chlorophenyl or 3,4-dichlorophenyl.

15. A compound having the formula (II):

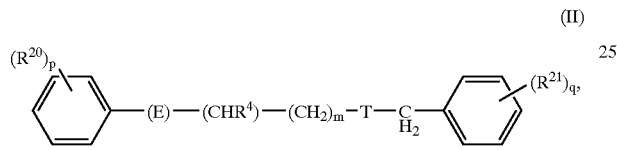

(II)

or a pharmaceutically-acceptable salt thereof, in which:
T is

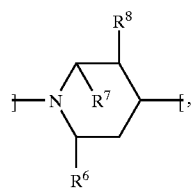

where R$^6$ is taken together with one of R$^7$ and R$^8$ to form a bridge one to two bridgehead carbon atoms optionally substituted with one to two CH$_3$, and the other of R$^7$ and R$^8$ is selected from hydrogen and lower alkyl;

E is selected from —C(=O)N(R$^{10}$)—, —N(R$^{11}$)C(=O)N(R$^{10}$)—, and —N(R$^{12}$)C(=O)CH(R$^{13}$)—, where:
R$^{10}$, R$^{11}$, R$^{12}$, and R$^{13}$ are independently of each other hydrogen or lower alkyl, or alternatively, R$^{12}$ and R$^{13}$ may be taken together with the nitrogen and carbon atoms to which they are attached, respectively, to form a five-membered heterocyclyl or heteroaryl ring having up to two N atoms and optionally substituted with up to two groups selected from methyl, ethyl, hydroxy, methoxy, halo, cyano, trifluoromethyl, and trifluoromethoxy;

R$^4$ is hydrogen, lower alkyl, or lower alkyl substituted with hydroxy;

R$^{20}$ and R$^{21}$ are each independently selected from halo, OR$^{22}$, and SO$_2$R$^{22}$, wherein R$^{22}$ is lower alkyl;

is 0 or 1;

p and q are independently 0, 1, 2 or 3.

16. A compound of claim 15, or a pharmaceutically acceptable salt thereof, wherein
E is selected from —C(=O)NH—, —NHC(=O)NH—, and

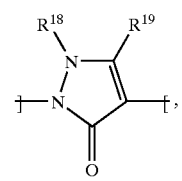

where R$^{18}$ and R$^{19}$ are each hydrogen or lower alkyl;

R$^4$ is hydrogen, methyl, ethyl, 1-hydroxyethyl, or 1-methylethyl;

R$^6$ is taken together with one of R$^7$ and R$^8$ to form a bridge of two bridgehead carbon atoms and the other of R$^7$ and R$^8$ is hydrogen;

R$^{20}$ is selected from halo, methoxy, and methylsulfonyl;

R$^{21}$ is halo;

p is 0, 1, 2 or 3; and q is 0, 1, or 2.

17. A compound of claim 16, or a pharmaceutically acceptable salt wherein T is

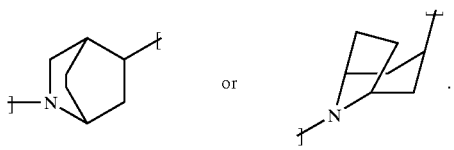

* * * * *

UNITED STATES PATENT AND TRADEMARK OFFICE
CERTIFICATE OF CORRECTION

PATENT NO. : 7,005,087 B2  
APPLICATION NO. : 10/748725  
DATED : February 28, 2006  
INVENTOR(S) : Tong It is certified that error appears in the above-identified patent and that said Letters Patent is hereby corrected as shown below:

Delete claims 1-17, and replace with claims 1-17 as attached.  
Col 10 - line 28 thru Col 14 line 47

Signed and Sealed this

Twenty-seventh Day of February, 2007

JON W. DUDAS  
*Director of the United States Patent and Trademark Office*

CLAIMS

1. A composition comprising (meth)acrylic acid and one or more of the compounds selected from the group consisting of aminoalkyl imidazolines of formula (I)

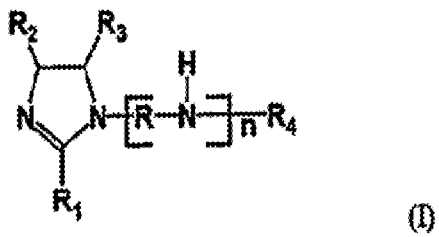

(I)

and alkyl-substituted succinimides of formula (II)

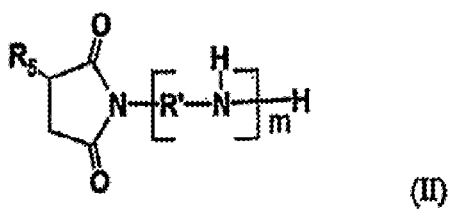

(II)

and mixtures thereof wherein n is an integer of 1 to about 9; m is an integer of 1 to about 10; R and R' are $C_1$-$C_6$ alkylene; $R_1$ $R_2$ $R_3$ and $R_5$ are independently selected from $C_1$-$C_{30}$ alkyl, alkenyl, aryl, alkylaryl, arylalkyl, aminoalkyl, and aminoaryl; and $R_4$ is selected from hydrogen, $(CH_2)_2COOH$, $CH_2CH(CH_3)COOH$, imidazoline, alkyl and alkylaryl.

2. The composition of claim 1 wherein the aminoalkyl imidazoline is prepared by reacting a carboxylic fatty acid with a polyethylene polyamine.

3. The composition of claim 1 wherein the aminoalkyl imidazoline is prepared by reacting tall oil fatty acid with a polyethylene polyamine.

4. The composition of claim 1 wherein the aminoalkyl imidazoline is prepared by (i) reacting tall oil fatty acid with a polyethylene polyamine; and (ii) reacting the product of step (i) with acrylic acid.

5. The composition of claim 1 wherein the alkyl-substituted succinimide is prepared by reacting a mixture of $C_{12}$-$C_{30}$ olefins, maleic anhydride and polyethylene polyamine.

6. The composition of claim 1 wherein the alkyl-substituted succinimide is prepared by reacting a mixture of $C_{12}$-$C_{30}$ olefins, maleic anhydride and diethylene triamine.

7. The composition of claim 1 further comprising one or more polymerization inhibitors.

8. The composition of claim 1 further comprising one or more dispersants.

9. The composition of claim 1 further comprising one or more polymerization inhibitors and one or more dispersants.

10. The composition of claim 1 further comprising one or more solvents.

11. A method of preventing fouling in a (meth)acrylic acid process comprising adding to the process stream an effective antifouling amount of one or more aminoalkyl imidazolines of formula (I)

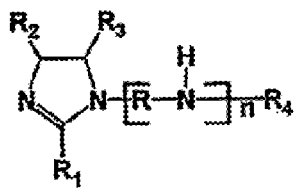

(I)

or one or more alkyl-substituted succinimides of formula (II)

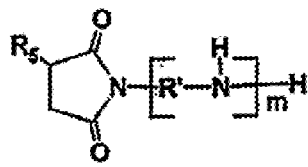

(II)

or a mixture thereof wherein n is an integer of 1 to about 9; m is an integer of 1 to about 10; R and R' are $C_1$-$C_6$ alkylene; $R_1$, $R_2$, $R_3$ and $R_5$ are independently selected from $C_1$-$C_{30}$ alkyl, alkenyl, aryl, alkylaryl, arylalkyl, aminoalkyl, and aminoaryl; and $R_4$ is selected from hydrogen, $(CH_2)_2COOH$, $CH_2CH(CH_3)COOH$, imidazoline, alkyl and alkylaryl.

12. The method of claim 11 wherein the aminoalkyl imidazolines or alkyl-substituted succinimides are added to the process at a dosage of about 1 to about 10,000 ppm.

13. The method of claim 11 wherein the aminoalkyl imidazolines or alkyl-substituted succinimides are added to the process at a dosage of about 10 to about 1000 ppm.

14. The method of claim 11 wherein the aminoalkyl imidazolines or alkyl-substituted succinimides are added to the process at a dosage of about 30 to about 300 ppm.

15. The method of claim 11 wherein the aminoalkyl imidazolines or alkyl-substituted succinimides are added continuously.

16. The method of claim 11 wherein the aminoalkyl imidazolines or alkyl-substituted succinimides are added intermittently.

17. The method of claim 11 wherein the (meth)acrylic acid process is selected from (meth)acrylic acid manufacturing processes, (meth)acrylic acid esterification processes, acrolein manufacturing processes and acrylonitrile manufacturing processes.